(12) United States Patent
Hughes et al.

(10) Patent No.: US 6,807,766 B1
(45) Date of Patent: Oct. 26, 2004

(54) ELECTRONIC PROGRAMMABLE FISHING LURE

(76) Inventors: Charles B. Hughes, 3309 Lookout Dr., Huntsville, AL (US) 35801; Emory D. Hughes, 46 High Point Rd., Edgefield, SC (US) 29824

(*) Notice: Subject to any disclaimer, the term of this patent is extended or adjusted under 35 U.S.C. 154(b) by 0 days.

(21) Appl. No.: 10/012,112

(22) Filed: Dec. 3, 2001

Related U.S. Application Data (63) Continuation of application No. 09/206,596, filed on Dec. 7, 1998, now Pat. No. 6,325,066, which is a continuation-in-part of application No. 08/918,455, filed on Aug. 26, 1997, now Pat. No. 5,845,644
(60) Provisional application No. 60/025,022, filed on Aug. 26, 1996.

(51) Int. Cl.$^7$ ............................................... A01K 85/01
(52) U.S. Cl. .................. 43/17.6; 43/17.1; 43/42.31; 43/42.22; 43/42.35; 43/42.06
(58) Field of Search ................. 43/17.5, 17.6, 43/17.1, 42.31, 42.22, 42.35, 42.06

(56) References Cited

U.S. PATENT DOCUMENTS

| | | | | |
|---|---|---|---|---|
| 3,025,628 A | * | 3/1962 | Murawski | 43/42.22 |
| 3,403,466 A | * | 10/1968 | Young | 43/42.06 |
| 3,762,092 A | * | 10/1973 | Bercz et al. | 43/17.6 |
| 4,550,521 A | * | 11/1985 | Hayden | 43/42.06 |
| 4,583,313 A | * | 4/1986 | Dugan, Jr. | 43/17.1 |
| 4,638,584 A | * | 1/1987 | Lindsay | 43/17.6 |
| 4,669,213 A | * | 6/1987 | LeRoy | 43/17.6 |
| 4,799,327 A | * | 1/1989 | Treon | 43/17.6 |
| 4,805,339 A | * | 2/1989 | Fuentes et al. | 43/42.31 |
| 4,823,497 A | * | 4/1989 | Pierce | 43/17.6 |
| 4,888,904 A | * | 12/1989 | Douglas, Jr. | 43/17.6 |
| 4,888,905 A | * | 12/1989 | Garr | 43/17.6 |
| 5,076,003 A | * | 12/1991 | Chen | 43/17.5 |
| 5,148,622 A | * | 9/1992 | Blair | 43/17.1 |
| 5,157,857 A | * | 10/1992 | Livingston | 43/17.6 |
| 5,175,950 A | * | 1/1993 | Linder | 43/17.1 |
| 5,175,951 A | * | 1/1993 | Fruchey | 43/17.6 |
| 5,177,891 A | * | 1/1993 | Holt | 43/17.1 |
| 5,330,282 A | * | 7/1994 | Rodgers | 43/17.6 |
| 5,331,760 A | * | 7/1994 | DuMont | 43/17.1 |
| 5,461,815 A | * | 10/1995 | Rodgers | 43/17.6 |
| 5,517,781 A | * | 5/1996 | Paoletta, Jr. | 43/42.06 |
| 5,697,182 A | * | 12/1997 | Rodgers | 43/17.1 |
| 5,725,892 A | * | 3/1998 | Gibbs | 43/42.06 |
| 5,758,450 A | * | 6/1998 | Young | 43/17.6 |

(List continued on next page.)

FOREIGN PATENT DOCUMENTS

| | | | | |
|---|---|---|---|---|
| AU | 9457701 | B1 | * | 9/1994 |
| DE | 19512031 | B1 | * | 10/1996 |
| FR | 2720894 | B1 | * | 12/1995 |
| GB | 2322530 | B1 | * | 9/1998 |
| GB | 2333431 | B1 | * | 7/1999 |
| JP | 10-33089 | B1 | * | 2/1998 |
| JP | 2001-17048 | B1 | * | 1/2001 |
| JP | 2002-199828 | B1 | * | 7/2002 |
| SE | 9100109 | B1 | * | 7/1992 |
| WO | WO-84/02446 | B1 | * | 7/1984 |
| WO | WO-95/03691 | B1 | * | 2/1995 |
| WO | WO-01/82690 | B1 | * | 11/2001 |

*Primary Examiner*—Darren W. Ark
(74) *Attorney, Agent, or Firm*—Mark Clodfelter

(57) ABSTRACT

A fishing lure or decoy is provided, the lure having a casement for receiving an electronic insert. The insert is operated by a microcontroller programmed to implement at least one sequence of operation implemented by at least one of a LED light emitter, a vibration-producing device and an audio transducer. An electrical power supply in the insert provides power to the devices and microcontroller, and a pair of externally exposed contacts switches the microcontroller ON when bridged by water containing electrolytes, as would be found in a fishing area. This also produces an electrical field around the lure, this electrical field also serving to simulate living food creatures to entice fish to bite the lure.

16 Claims, 9 Drawing Sheets

U.S. PATENT DOCUMENTS

| | | | |
|---|---|---|---|
| 6,098,331 A | * | 8/2000 | Kim et al. .................... 43/17.6 |
| 6,108,962 A | * | 8/2000 | Barron ...................... 43/42.31 |
| 6,192,617 B1 | * | 2/2001 | Lyles ........................ 43/42.06 |
| 6,564,497 B2 | * | 5/2003 | Jackson, II ................... 43/17.1 |
| 6,581,319 B2 | * | 6/2003 | West .......................... 43/17.1 |
| 2003/0182841 A1 | * | 10/2003 | Calak et al. ................. 43/17.6 |

* cited by examiner

ELECTRONIC PROGRAMMABLE FISHING LURE

CONTINUING APPLICATION DATA

This application is a continuation-in-part of patent application Ser. No. 09/206,596, filed Dec. 7, 1998 now U.S. Pat. No. 6,325,066, which is a continuation-in-part of patent application Ser. No. 08/918,455, filed Aug. 26, 1997 now U.S. Pat. No. 5,845,644, which claims the benefit of provisional patent application Ser. No. 60/025,022, filed Aug. 26, 1996.

FIELD OF THE INVENTION

This invention relates to fishing lures and decoys, and particularly to an electronic fishing lure having a microcontroller therein for activating one or more of several programmed modes of operation, and which is automatically activated upon contact with water.

BACKGROUND OF THE INVENTION

Fishing lures have been around for many years, and in the past have taken many forms, a typical lure having at least one fishing hook disguised or attached to something to entice food or game fish to bite at. As most of these fish are predatory in nature, i.e. secondary or even tertiary consumers, lures most often take the form of some sort of food for the fish to be caught. Such lures may be configured as frogs, crayfish, worms, other small fish and the like, and are typically successful when pulled through the water with a jerking motion or other motions to simulate a swimming frog or crayfish. Other lure devices, such as spinners, spoons, poppers, etc., are constructed of a shiny material and designed to be noisily dragged fairly rapidly across the surface of a fishing area to simulate an injured or fleeing critter that might be good for a predatory fish to eat.

One problem with these lures is that for the most part, they are inanimate objects and rely on skill of the fisherman pulling it through the water in order to simulate food for the fish. Where the fisherman is inexperienced at dragging the lure through the water or conditions are not right for the fish to feed, then the fish simply will not bite at the lure. In other instances, the fish become acclimated to lures, and learn to distinguish between a lure and food. As a result, there is a need for a lure that is more alluring to fish so as to cause them to bite at a lure under sub-optimal conditions.

Accordingly, it is one object of the invention to provide a fishing lure that more closely simulates living food for the fish to be caught. This is done by providing a variety of modes of electronic operation of the lure which may include light visible to the fish, vibration that the fish may feel, sound that the fish may hear and an electrical field around the lure that simulates an electrical nerve field of a living animal. A microcontroller may be used with any or all of the above features to sequence them in any order, and may include pauses between operation of the various modes. Other objects of the invention will become clear upon a reading of the following specification.

SUMMARY OF THE INVENTION

A fishing lure which may be configured as a frog, small fish, crawfish or any other fishing lure is provided, the lure used as a casement, housing or the like for an insert of the invention. The insert forms a watertight housing with an electrical power supply therein, and circuitry in the insert coupled to the power supply. Also coupled to the circuitry is an electrical device that when energized, makes the casement more attractive as bait to a fish. For activating the circuitry and the device, a pair of contacts serves to switch the circuitry and associated device ON when the contacts are bridged by water.

DETAILED DESCRIPTION OF THE DRAWINGS

Figure 1:
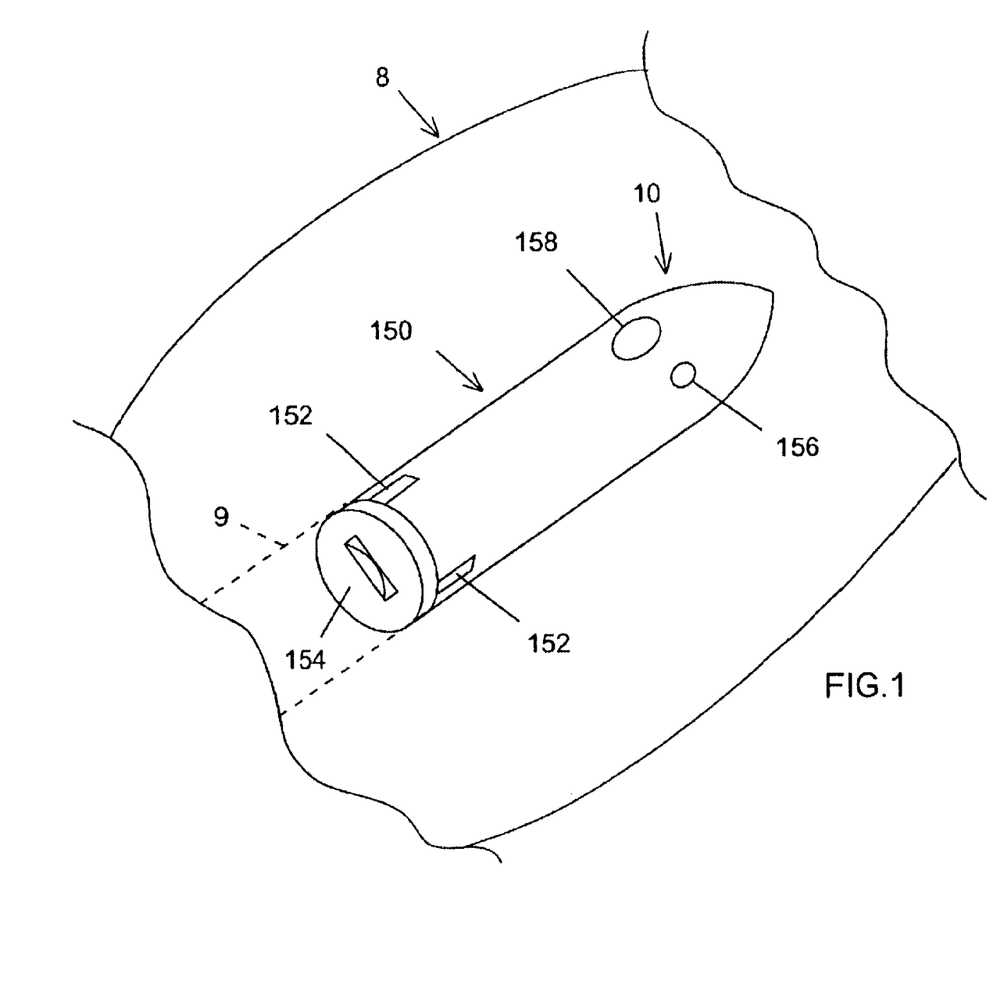
FIG. 1 is an illustration of an insert of the present invention.

Applicants have provided, in a most basic embodiment as shown in FIG. 1, an insert that may be placed into a soft-bodied fishing lure or other type of fishing lure that may serve as a casement, the lure configured as a worm, frog, fish, or any other type of fishing lure. In this embodiment, the insert may simply be pushed into the soft, transparent or translucent plastic, rubber or rubber-like material, or other materials such as hollowed wood, hard plastic or the like forming the casement, leaving a tunnel-like aperture therein, or attached to a rigid lure by any conventional means known in the art, such as glue, fasteners, etc. In other embodiments, the lure casement itself may be specifically configured to receive the insert and be combined with other features consistent with a fishing lure, such as coloration and markings representative of gill slits, eyes, and the like. In this instance, and as the insert includes at least one LED as one attractant mode of operation, light guides 200 (FIG. 2) may be molded or inserted into the casement to simulate glowing features thereof, such as eyes, gills slits, etc. Alternately, open, tunnel-like paths communicating with the LED may be molded into the casement to form walls from which light from the LED is reflected, again simulating glowing eyes, gill slits, etc. To this end, and as shown in FIG. 3, the insert itself may be provided with a dark-colored rearward portion 202, with a front portion 204 constructed of a clear or translucent material in order to transmit light from the LED. In addition, the clear or translucent portion of the insert may be faceted such as to direct light from the LED in multiple directions. In an adaptation of this embodiment, flexible fiber optic light guides may be used to form a skirt around the lure, with an interior end of each of the fiber light guides being molded into the casement proximate the LED. In another adaptation, a generally opaque covering may be placed over the insert, the covering having transparent regions proximate the LED to simulate glowing eyes or other features.

Figure 2:
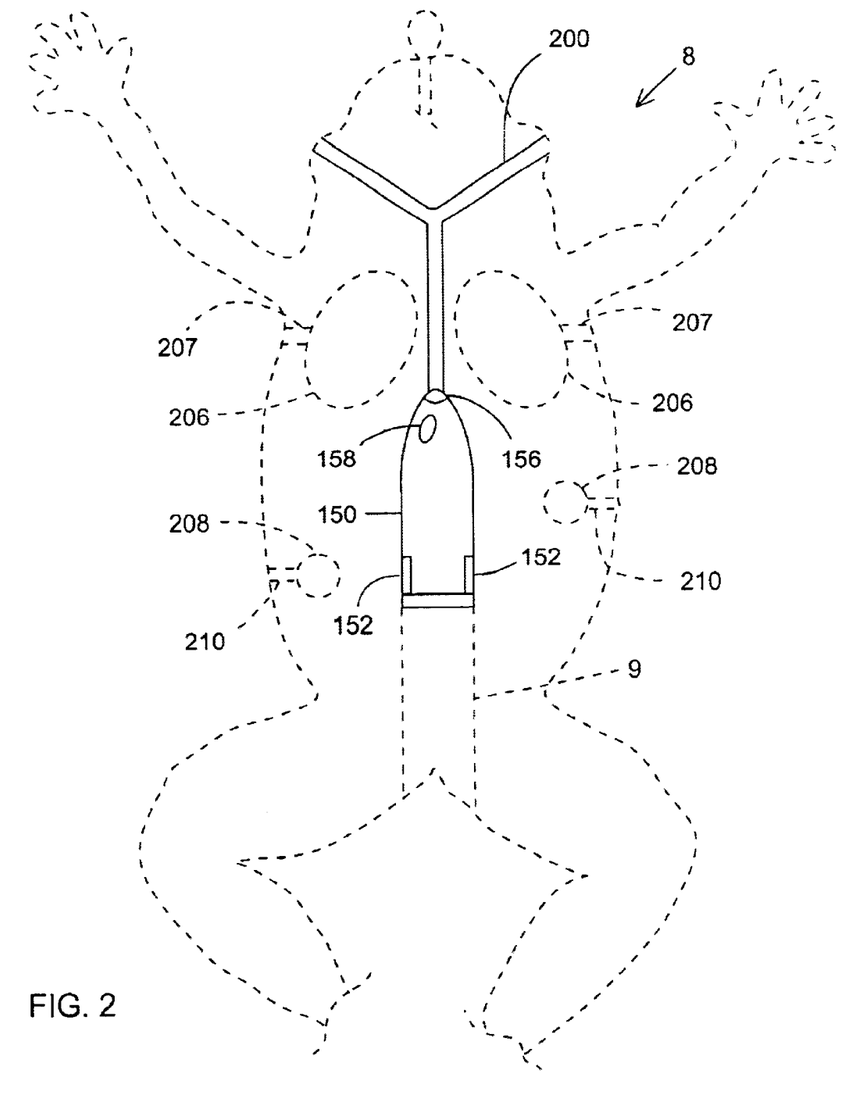
FIG. 2 is a diagrammatic illustration showing the insert of FIG. 1 inserted in a frog-like fishing lure.
Figure 3:
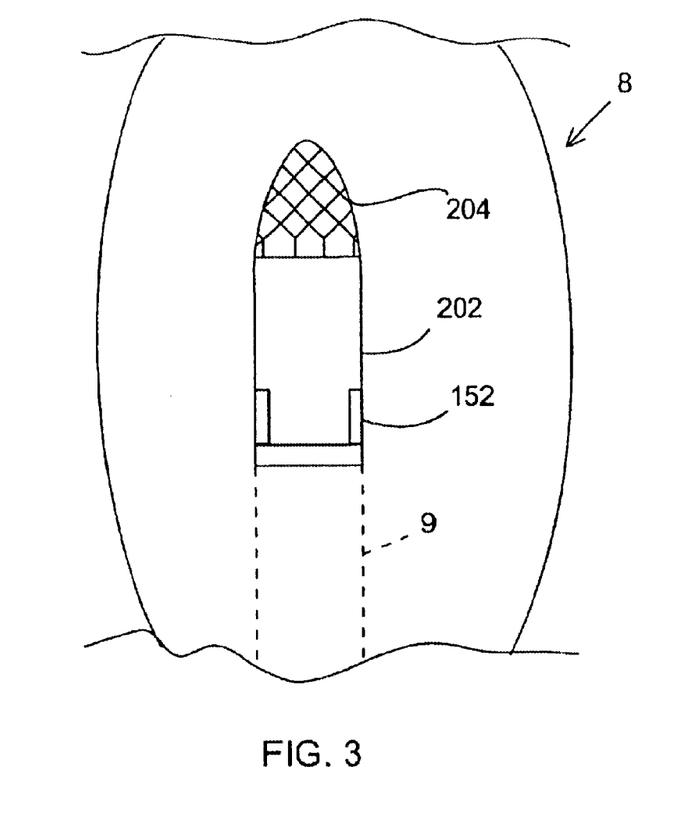
FIG. 3 is an insert of the present invention having a jewelled end for scattering light in a multitude of directions.

As another feature of the invention, and referring to FIG. 2, the lure itself may be constructed having one or more air ballast pockets 206 in order to offset weight of the insert to insure that the lure remains in a proper or selected orientation as it is pulled through the water. Also, air pockets 206 may be increased or decreased in size, as by injecting or removing air into/out of the air pockets, as by a syringe, in order to cause the lure to float at a selected depth. This is facilitated by the lures being constructed of the soft, flexible plastic material as described, which would generally be self-sealing with respect to small punctures such as those made by a syringe. Alternately, slits or openings 207 may be formed over pockets 206 and communicate therewith so that air may be admitted into or removed from the air pockets simply by squeezing the lure so that the slits open and close in a similar manner as a plastic change purse. In yet another embodiment, a small opening communicating with air pockets 206 may be used to release or admit air into the pockets. Here, a user would simply squeeze the lure in one direction to expel air from the pockets and squeeze the lure in an opposite direction to draw air into the pockets.

In another adaptation, cavities 208 may be formed in the lure within which a bait scent pellet or liquid may be placed, with a small opening 210 communicating with the external environment of the lure. This embodiment is useful where one mode of operation of insert 150 includes vibration, as such a vibration would stimulate release of the bait scent compound.

Figure 4:
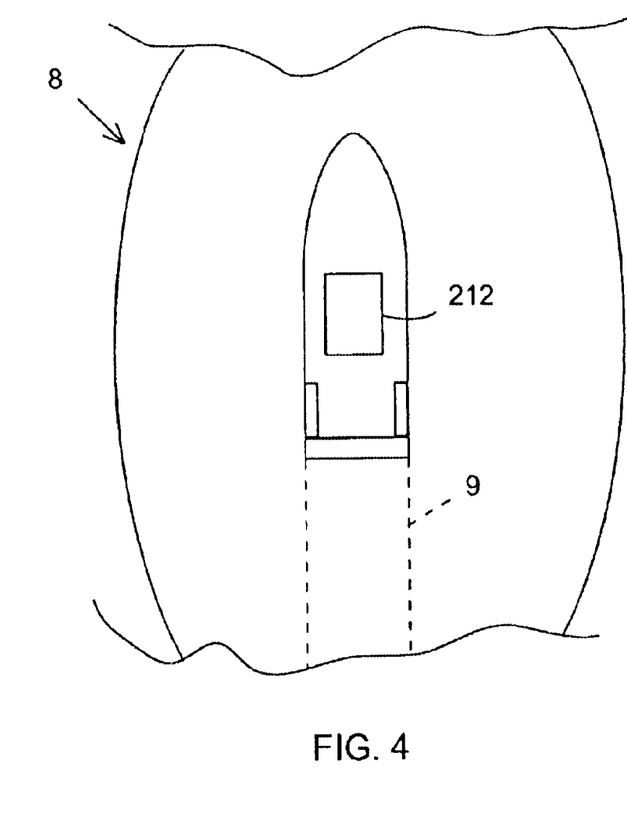
FIG. 4 is an insert of the present invention provided with an indicator on a side thereof.

In another feature as shown in FIG. 4, the insert may be provided with a temperature indicator 212 for indicating temperature of the water. This may be accomplished simply by mounting an LCD indicator similar to those found for indicating temperature in fish tanks on the body of the insert. Likewise, an indicator for indicating a maximum depth may be incorporated in the insert. Such a depth indicator may be constructed of silicon, and is available from B. F. Goodrich Advanced Micro Machines, part number LN-100. In this instance, a maximum depth would be stored in memory cells and provided to a digital readout on the lure. Resetting of the depth indication may be manual, or occur automatically after a preset time interval.

In yet another modification, the body or end cap of the insert 150 may be configured with wings or propellers that cause it to function as a spinner bait, buzz bait or similar noise-producing bait. In this embodiment, features such as an audio transducer. and vibration-producing device may not be needed as these functions are inherent in a spinner bait lure. In any embodiment having a spinner bait-like propeller, the rotary motion generated thereby may be coupled to a small electric generator coupled to exterior contacts of the lure. This would generate an electric field around the lure as it is pulled through the water, advantageously attracting predatory game fish. Alternately, electricity so generated may also be used to charge an internal battery or capacitor so that the insert may be completely sealed against water leakage. Other methods may be used to charge batteries or a capacitor such as solar cells or thermocouples. In addition, a rechargeable battery in the insert may be charged electromagnetically by putting the insert inside an induction coil such as those used for electric toothbrushes. Of course, where a shaft is used to couple the rotary motion, a seal is used to seal the shaft. Further yet, a magnetic coupling may be used between a propeller and tiny generator in the lure. In these embodiments, strength of the electric field would be directly related to speed of the lure as it is pulled through the water, thus simulating an electrical field of a fleeing animal, such as a frog.

The lure inserts of the present invention are energized when water containing electrolytes or other conductive substances bridges a pair of contacts exposed to the water. Such a mode of energization of the lure provides an electrical field simulating living organisms that are normally food for a predatory game fish. Once energized, a number of operational modes may be provided. These modes may include an audio mode, a blinking or other illumination mode, a vibration mode, or any other modes as required for the specific application. Typically, a sequence of three modes, including pauses, would be controlled by a microcontroller circuitry in the insert.

Figure 5:
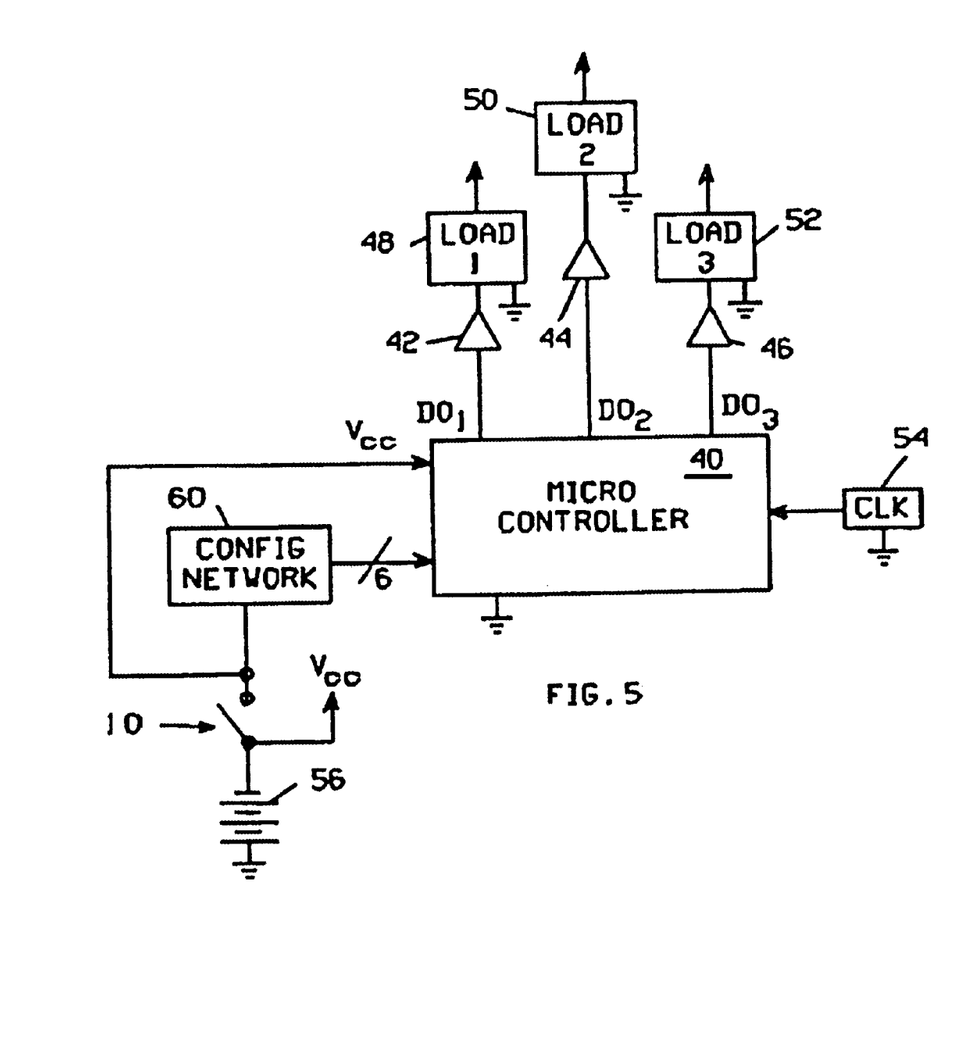
FIG. 5 is a block diagram of one example of circuitry for operating the insert of the present invention.

Referring now to FIG. 5, and by way of example, a block diagram of one microcontroller-based system is shown which may be used to control electrical operation of the instant invention. Here, three outputs 48, 50, and 52 labeled load 1, load 2, and load 3 are shown for a microcontroller which may implement one or more of 3 modes of operation. These loads may be a vibrator for providing vibration, an audio transducer for providing an audible tone or other audio signal, and a light indicator for providing a visible indication, such as from an LED indicator. Additionally, an RF transmitter may be energized responsive to a wetted condition of the contacts to transmit an RF signal to a receiver or receivers for sending a signal indicating that the device is activated. Other transmitted signals may provide temperature and depth information.

Operation of insert 150 may be based on a microcontroller 40, for example one of the PIC16C family of microcontrollers, manufactured by MICROCHIP, located in Chandler, Ariz. These microcontrollers have up to 2K bytes of ROM memory, which may be used to store a system program, and up to 72 bytes of RAM memory, which may be used to store program variables during timing operations. Additionally, as this microcontroller family is of CMOS technology, its low power consumption (less than 2 ma at 5 VDC clocked at 4 MHz) is ideal for battery powered applications. In this embodiment, it is contemplated that microcontroller 40 and related components may be powered by 3 volts supplied by a pair of coin-type batteries, or 4.5 volts supplied by three such batteries, as should be apparent to those skilled in the art. Alternately, any other suitable microprocessor and battery combination may be used in order to meet cost, performance and production needs.

An oscillator 54 provides a train of clock pulses to microcontroller 40 at any rate up to about 20 MHz or so. Power may be provided via contacts 152, which are illustrated in FIG. 5 as a switch 10, from batteries 56 to configuration network 60. Network 60, which may be coupled to data input lines of microcontroller 40, is configured to activate particular ones of data outputs DO1, DO2, and DO3 for selected time intervals, and thus constitutes a portion of a program of operation for microcontroller 40. In another embodiment, a sequence of modes of operation of the various devices for attracting fish may be permanently incorporated in the circuitry by using a microcontroller with a larger read-only memory or separate ROM containing the program, or by sealing the circuitry with network 60 permanently set and not accessible to the user.

Figure 6:
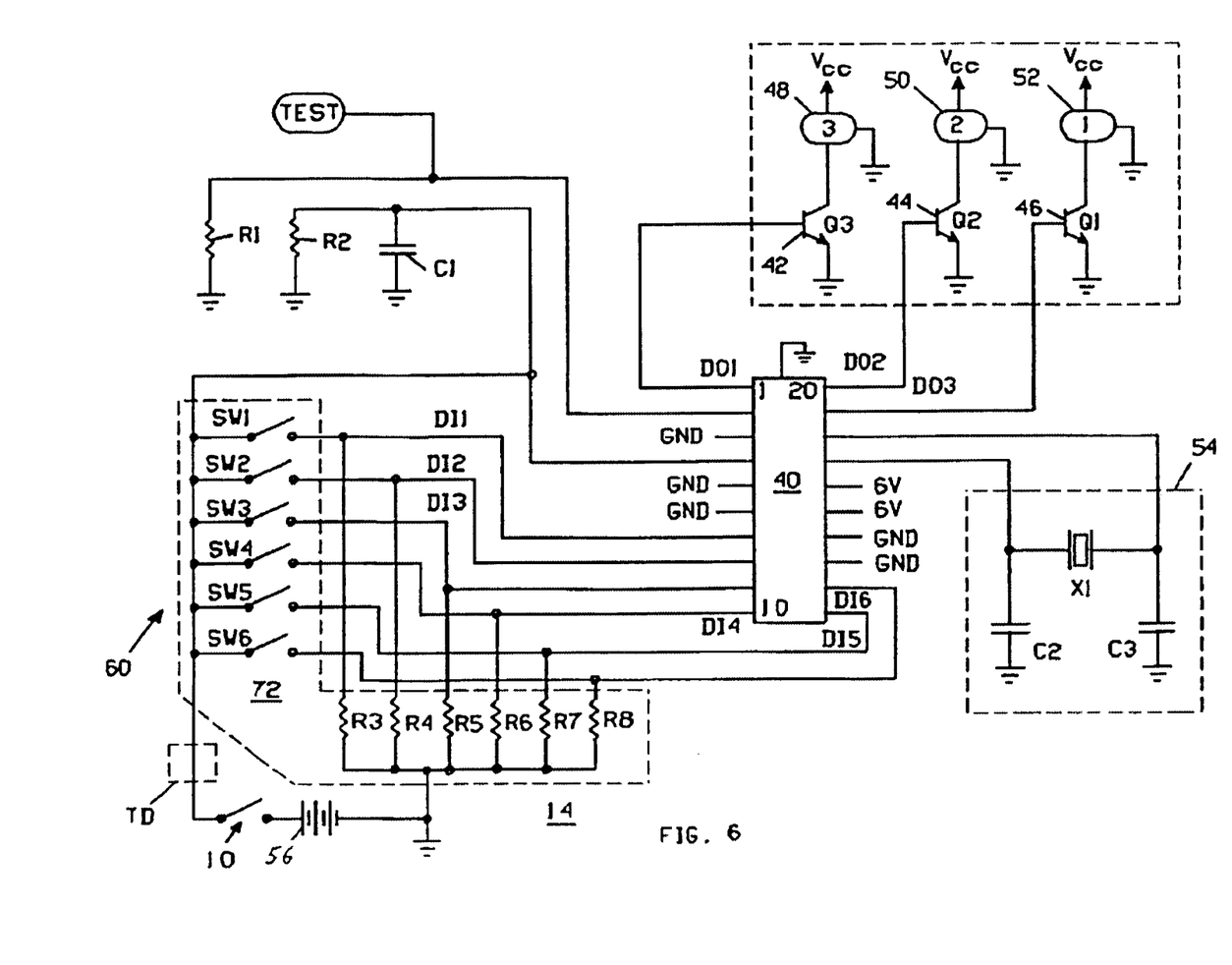
FIG. 6 is a schematic diagram of the block diagram of FIG. 5.

Referring now to FIG. 6, a detailed schematic of the block diagram of FIG. 5 is shown. In this schematic, it is seen that, upon closure of the contacts, power and a reference ground potential are provided by battery 56 to microcontroller 40 and all components requiring such potentials. Here, battery power is applied to one contact of switch 10, with the other contact coupled to configuration network 60, the power input of microcontroller 40, and distributed to other components requiring power. Network 60 may include a miniature DIP switch 72 incorporating a plurality of switches, such as 6 switches, these switches coupled between the switched conductor and a respective one of data inputs DI1–DI6 of microcontroller 40. Coupled between each of DIP switches 72 and the ground reference potential are resistors R3–R8, which serve to develop a voltage drop sufficient to trigger the respective inputs of microcontroller 40. Here, where a higher value of resistance is selected for resistors R3–R8, less current flow through the contacts would be sufficient to trigger the respective inputs of microcontroller 40, and conversely, where a lower value for these resistors is selected, more current flow would be required through in order to develop a sufficient voltage drop to trigger the inputs of microcontroller 40. Thus, sensitivity of the system may be adjusted by varying resistances of resistors R3–R8. By way of example, these resistors may be in the range of about 100K ohms, this selection being fairly sensitive to electrolytes and very conservative of battery power. In order for the DIP switches to be accessible to a user, the entire circuit board on which the electronic components, including the DIP switches, may be mounted may be removable from the insert through the battery opening. Slots or grooves may be provided along the inside of the insert so that the circuit board is securely held in place in the insert when in use. In other embodiments, the switches of network 60 may be configured as jumpers, or where the program is permanently set, as traces in the circuit board that are selectively cut during assembly. Here, a number of lures may be commercially provided, each having a different program of operation according to specific needs of fishermen purchasing the lures.

In yet other embodiments, an oscillating or other signal may be applied to one of the conductors 152, with the other conductor coupled to a detector for detecting the oscillating signal when the conductors are bridged by conductive fluid. A HIGH logic level would then be provided to network 72 by the detector, activating the loads as described. Also, an adjustable or nonadjustable time delay TD (dashed lines) may be located between strip switch 10 and the rest of the circuitry associated with the microcontroller so that upon expiration of the time delay, power is applied to the microcontroller and a HIGH logic level applied to network 72. Alternately, a slower clock pulse may be used in conjunction with a counter and latching decoder to implement the time delay, with the decoder providing a latched output to power the microcontroller and network 72 responsive to a selected count. As such, and with closure of selected ones of the switches of network 72, when the conductors are shorted by a conductive fluid, configuration information is provided to microcontroller 40 through DIP switches 72, this configuration information controlling sequencing and duration of outputs DO1, DO2, and DO3.

The program loaded in ROM memory of microcontroller 40 may use data inputs DI1–DI3 to select which of loads 48, 50, and 52 are to be activated, respectively, with data inputs DI4–DI6 selecting time delays and sequencing of activation of the loads. Constructed as described, and with 6 switches in network 72, 16 distinct operating modes are made available to the user. The three outputs DO1, DO2, and DO3 may be normally LOW with a common ground, and when activated by the microcontroller, will transition HIGH, enabling the respective one of loads 48, 50, and 52 through a respective buffer amplifier. Where time delay functions are enabled, delays may be selected in increments, such as seconds or milliseconds, after which sequencing of the loads is initiated. After the program sequencing the loads is completed, the microcontroller may be placed in a "sleep" mode in order to conserve battery power.

As described, loads 48, 50, and 52 are activated by data lines DO1 controlling load 1, DO2 controlling load 2, and DO3 controlling load 3 via buffer amplifiers 42, 44, and 46, respectively. As stated, load 48 may be a vibrator, load 50 may be an audio signal, and load 52 may be a LED indicator. In the latter instance, a LED having an internal current-limiting resistor or internal circuitry for causing the LED to blink may be used, or an external current-limiting resistor (not shown) may be used. Alternately, one of the loads may be coupled to a short-range radio transmitter, such as one transmitting in the 902–928 MHz Industrial, Scientific, and Medical (SM) range and which may use multiple frequencies in this range, for notifying a user of activation of the device or sending other data, such as temperature and depth.

Figure 7:
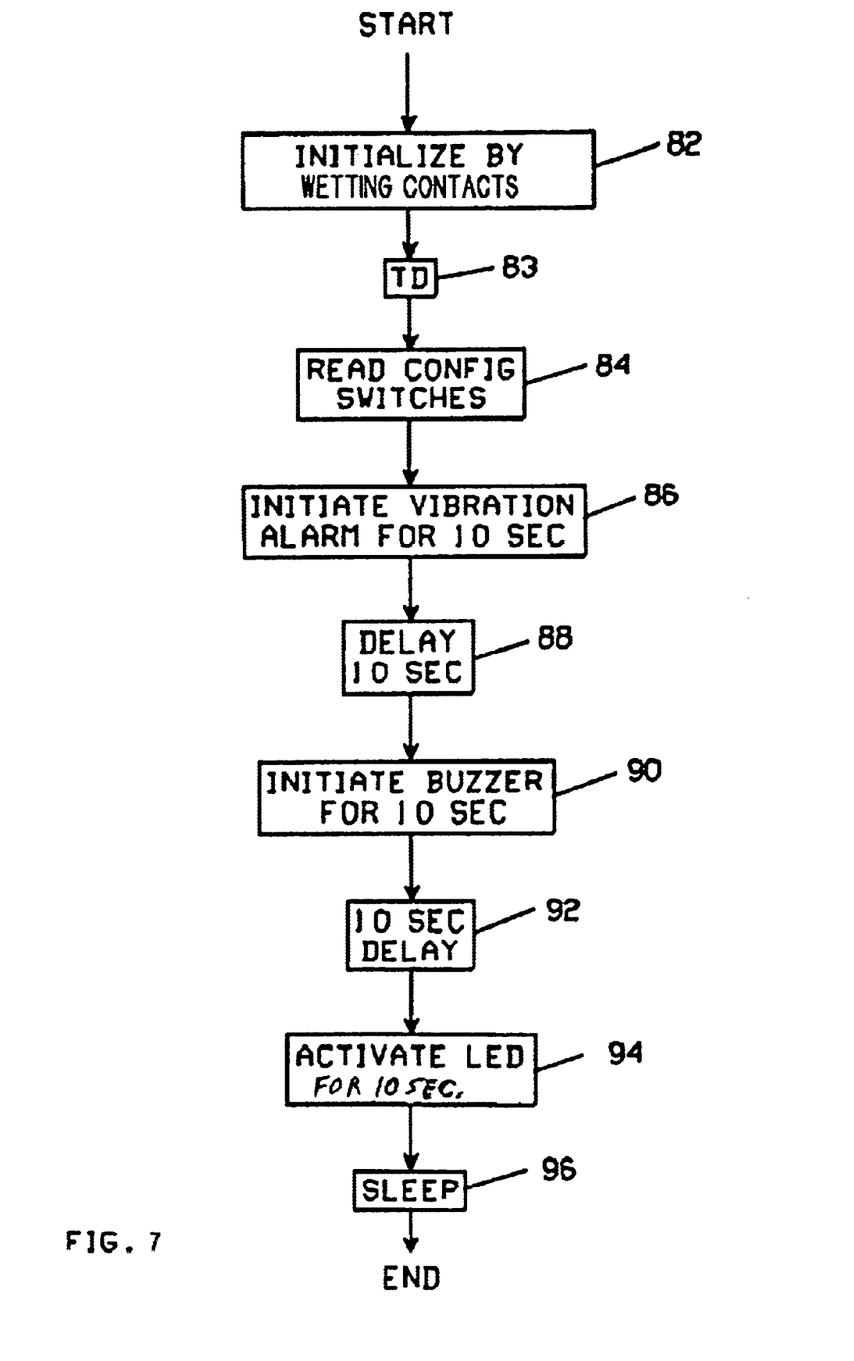
FIG. 7 is a flowchart of one possible mode of operation of the insert of the present invention.

The ROM memory of microcontroller 40 is loaded with a program, which may be written in RISC (reduced instruction set computer) language to perform the various functions of the system, an example of one program being shown in the flowchart of FIG. 7. Here, unit 14 is unpowered until the conductors 152 are bridged, effectively closing sensor switch 10 as shown at box 82. This feature greatly conserves battery power; the circuitry contained in package 14 being unpowered until switch 10 is closed. When energized, microcontroller 40 is initialized as indicated at box 82, clearing and initializing all registers to a predetermined value as is known to those skilled in the art. After power-up initialization of microcontroller 40, the program directs configuration switches 72 (or program data retrieved from ROM memory) to be read at box 84, and an output or outputs to the loads provided based on the settings of configuration switches 72. As shown at box 86, for example, load 48, which may be a vibrator motor, may be initially energized to provide a silent, vibratory indication. After a duration which may be about 10 seconds or so, the vibration motor is de-energized, and a time delay of about 10 seconds or so may be initiated at box 88. After the delay at box 88 expires, the program proceeds to box 90 where load 50 may be energized, which load may be an audio signal such as a buzzer, which may be energized for about 10 seconds, after which another time delay of about 10 seconds may be initiated at box 92. After the time delay of box 92 expires, the program proceeds to box 94 where load 52, which may be an LED indicator, may be energized for a duration which may be about 10 seconds or so. After this delay expires, the program may direct microcontroller 40 to enter a power-conserving sleep mode for a longer period of time, such as 20 seconds of so as indicated at box 96, and then wake up to repeat the program. Upon removal of the bridge between the contacts, i.e. the lure is taken from the water, power is removed from microcontroller 40, resetting controller 40 in preparation for the next cycle.

While a specific program using all three modes of operation is provided, it should be clear that not all modes of operation are needed for a successful lure. For instance, the device may be programmed so that the LED blinks at timed intervals, or simply remains ON while the lure is in the water. Likewise, the device may be programmed to energize the audio transducer with a constant or varying tone followed by energization of the vibration device. In conjunction with the electrical field, such a lure should prove very effective. Thus, any sequencing of the audio transducer, vibrator and LED, including pauses between the various functions, may be implemented by appropriately configuring the program as described. In addition, the lure may be constructed having fewer than the described modes of operation available, such as a lure having just the LED and a vibrator.

Figure 7A:
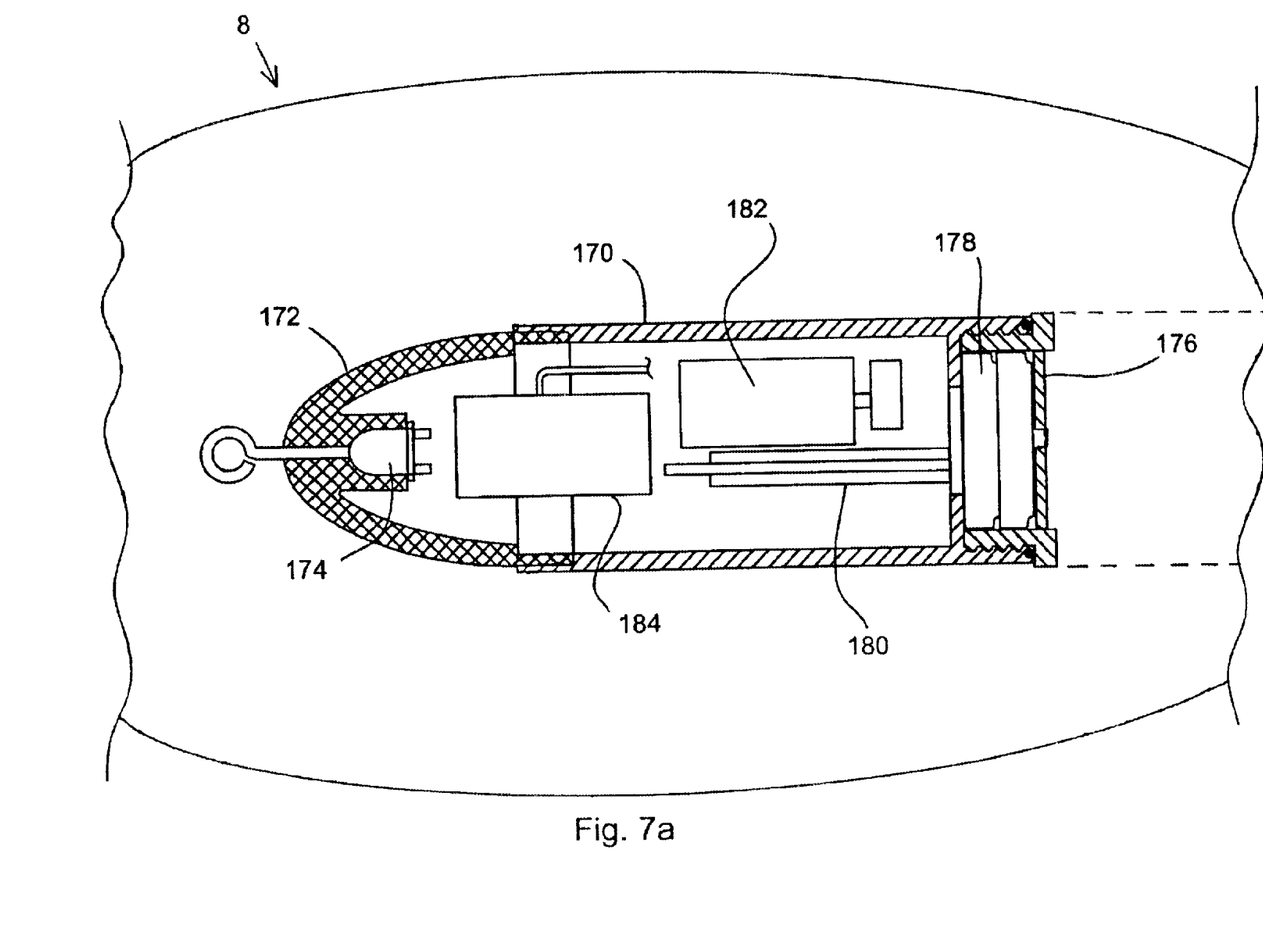
FIG. 7a is an illustration of one possible layout of an insert of the present invention.

FIG. 7a shows one possible layout of an interior of an insert of the present invention. Here, a housing 170 includes a transparent or translucent nose or end 172 that distributes light from an LED 174. At an opposite end, a threaded battery cap 176 having a seal, such as a O-ring, sealably caps a battery compartment 178 housing a plurality of coin-type batteries. The batteries conventionally are coupled by contacts to a printed circuit board 180 to which the electronic components are mounted, and a miniature vibrator may be mounted adjacent the printed circuit board. The audio transducer may be mounted as shown between the LED and printed circuit board. Structural supports may be used to support the components, or some components may be permanently potted or glued into place. Wiring connecting the components may be routed as required.

In a variant of this invention, a lure retrieval device may be constructed shaped similarly to the insert of FIG. 1, except it would be of much heavier construction. In addition, it would have provisions to slidably and removably clip to a fishing line so as to enable it to slide theredown and impinge against a fishing lure snagged on a submerged object, hopefully dislodging the lure. In the event the impact does not dislodge the lure, a vibrator motor is provided and energized to vibrate against the snagged lure in order to vibrate it loose from the snagged condition. In this embodiment, the program need only to repeatedly cycle a vibrator motor ON and OFF for selected intervals of time, such as 2 seconds ON, one second OFF, and so forth, or simply remain energized while in the water. As described above, when the lure retrieval device is removed from the water, it is automatically deenergized. In addition, it should be clear that the vibration motor or other vibration-producing device is of heavier construction than a vibrator in the lure insert so as to produce sufficient vibration to dislodge the lure, and the power supply (batteries) are larger than those in the lure insert in order to power the larger motor.

Figure 9:
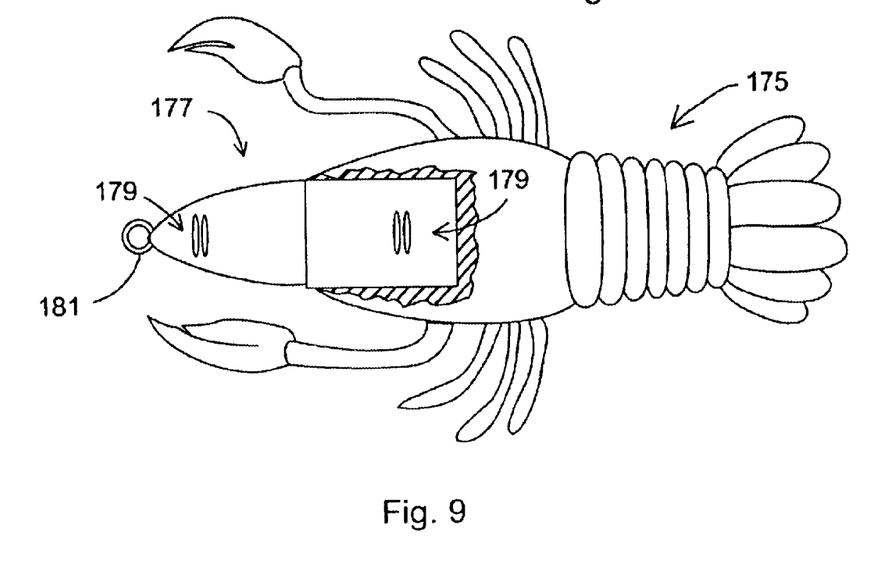
FIG. 9 is an illustration of a lure retrieval device configured as a crayfish lure.
Figure 10:
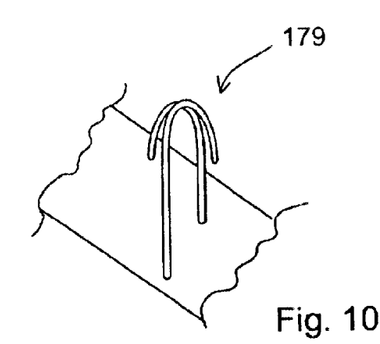
FIG. 10 is an illustration of how the lure retrieval device may be slidably attached to a fishing line.

Configuration of one such device, by way of example, is shown in FIGS. 9 and 10. As shown, a rearward portion 175 may be configured as a lure, such as a crayfish, with a forward portion 177 being the forward portion of the lure retrieval device protruding from the lure portion. Of course, the lure portion is firmly bonded or otherwise attached in the retrieval device so as not to become detached therefrom. The casing of the lure retrieval device may be constructed in two portions and threadably attached, as shown by dashed lines, so as to provide access to change the batteries therein. As shown in FIG. 10, the lure retrieval device may be slidably attached to a fishing line by at least one pair of opposed and closely spaced hooks 179. The fishing line would simply be slid into place between the hooks and rotated 90 degrees so that the retrieval device is suspended by the hooks and is able to slide on the line. As shown in FIG. 9, two pairs of hooks 179 are used to stabilize the retrieval device so that it slides down a fishing line in a head-first orientation to ensure that the hard, forward portion 177 of the retrieval device impinges against a snagged lure. A loop 181 is fixed to the lure retrieval device, and is used to attach a retrieval line to the retrieval device for retrieving the device in the event the lure remains snagged, necessitating that the fishing line be cut or is unintentionally broken. In addition, the retrieval device may be used as a lure by having a hook attached to ring 181. In this instance, the retrieval device may be used by itself as a lure, or become a lure as it is used to retrieve a snagged lure. In the event a fish becomes hooked on the retrieval device, the fish itself may assist in loosening a snagged lure through its pulling on the fishing line. Here, the fish hooked on the retrieval device may also be caught by the fisherman pulling the fish in by pulling on the retrieval line.

In yet another embodiment of the invention, a time-based microprocessor generally as described above, along with appropriate software, may be incorporated into a wristwatch type multiple alarm device (preferably with 5 alarms) to be worn on the wrist or a pendant that may be worn around the neck. In this instance, any of the modes of operation as discussed above, preferably audio and vibration, may occur in any sequence desired to serve as alarms, except the modes of operation would not be programmed by a network 60. Instead, the watch would have two exterior buttons to set the alarms, the time and modes of operation of the alarms. Of course, a conventional electronic timepiece would also be incorporated in the watch. This type of alarm device serves as a reminder where particular exercises, such as Kegal exercises, bowel and bladder exercises or any other exercise is to be done at intervals throughout the day. Also, instead of a wrist-worn device, the time based microprocessor may be incorporated into a pocket or purse-carried device. Particularly, the case of a pendant or strap or case of a watch may be configured having removable buttons, sliding indicators or other indicators for reminding a user that an event has occurred. Here, where a user is to take medication one or more times a day, and on a particular schedule, an indicator on the watch or pendant may be set at the time the medication is taken. This would serve to prevent doubling of doses by reminding the user that the scheduled dose has been taken. In another application, such a watch or pendant may be used to remind a user that it is time for exercises of a therapeutic nature, such as Kegal exercises, are to be done. Alternately, a button on the watch may be used to set an electronic indicator, such as an LCD or LED indicator. As such, when an alarm, which may be audible, visible, or vibrating, is indicated, the user would move a snap from one side of the watchband to the other, move a sliding indicator or press a button on the watch to set the electronic indicator.

Figure 8:
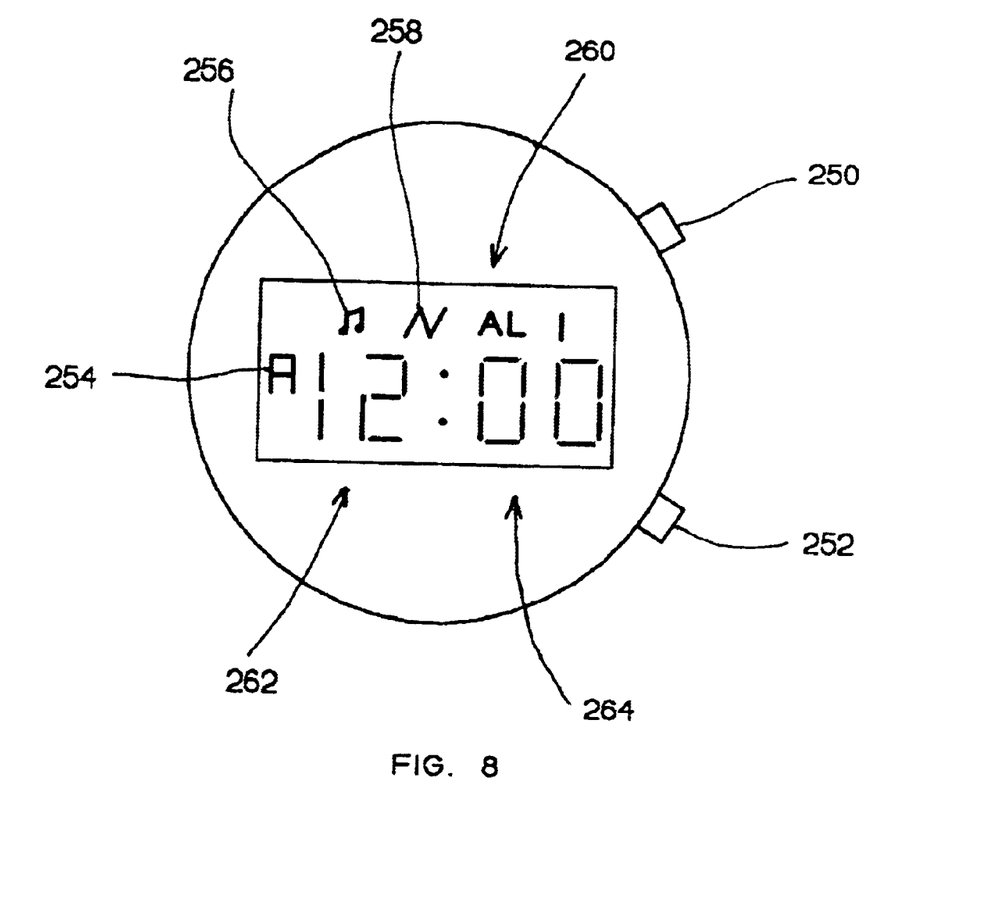
FIG. 8 is an illustration of a 5-alarm watch.

Referring to FIG. 8, one such contemplated watch is shown by way of example. A SET button 250 and a MODE button 252 is used for setting time, alarms and a mode of operation. On the face of the watch is an AM/PM indicator 254, an alarm beep indicator 256, an alarm vibration indicator 258, and an alarm number 260. Conventionally, hours 262 and minutes 264 are provided, preferably in large LCD numbers for ease of reading.

For setting the watch, the SET button 250 is pressed and held down (for about 2 seconds) until the hour display 262 flashes. The MODE button is then pressed until the correct hour in the PM or AM is displayed, at which point the SET button 250 is again pressed to lock in the correct hour setting. This also causes the minutes 264 to start flashing, and the MODE button 252 is likewise used to set the minutes. When the minutes are set correctly, the SET button 250 is pressed and the display stops flashing, indicating that the time is set. After the time is correctly set, the alarms may be set. Here, the SET button 250 is pressed and immediately released, causing the watch to enter the alarm set mode, as indicated by AL1 being indicated at 260. The SET button is then held down for about 2 seconds, causing the hour to flash, indicating it is ready to be set. The MODE button 252 is then used to set the hours (paying attention to the AM/PM indicator), after which the minutes begins to flash. The MODE button 252 is then used to set the minutes. For setting other alarms, the MODE button 252 is pressed once while the watch is in an alarm setting, and the watch switches to AL2, AL3, AL4 or AL5, after which entering the alarm setting mode as described may be respectively set as described above. Any of the alarms may be turned ON or OFF by pressing the SET button 250 once for an audio alarm, twice for vibration and three times for both. These respective alarms being ON are indicated by the indicators 256 and 258 being visible. After all the desired alarms are set, the MODE button 252 is repeatedly pressed until the AL position 260 is no longer visible. To check the alarms, the MODE button may be pressed to respectively cycle through the alarms, with the display showing the alarm time, the indicators 256, 258 showing the type of alarm and the AL position 260 showing the alarm number.

Having thus described my invention and the manner of its use, it is apparent that incidental changes may be made thereto that fall within the scope of the following appended claims, wherein I claim:

1. A fishing lure comprising:
    a casement configured as a fishing lure, the casement comprising a soft, transparent or translucent material or a hard material,
    a discrete, separate watertight housing insertable into said soft, transparent or translucent material, leaving a tunnel-like aperture in said soft, transparent or translucent material of said casement after insertion of the housing, or into a tunnel-like aperture formed in said hard material of said casement, said discrete, separate watertight housing containing an electrical power supply, circuitry coupled to said electrical power supply and at least one electrical device operated by a microprocessor so that when said at least one electrical device is energized said casement becomes more enticing to fish,
    a pair of contacts on said housing and positioned so as to be exposable to water in said tunnel-like aperture after said housing is inserted in said casement, said contacts coupled to said circuitry so that said circuitry is energized to operate said device upon said contacts being bridged by water containing electrolytes.

2. A fishing lure as set forth in claim 1 wherein said at least one electrical device comprises a vibration motor to produce vibrations of said casement.

3. A fishing lure as set forth in claim 2 wherein said at least one electrical device comprises at least one light emitting diode.

4. A fishing lure as set forth in claim 3 wherein said casement is provided with light guides from said at least one light emitting diode to features on said casement to be illuminated by light from said at least one light emitting diode.

5. A fishing lure as set forth in claim 2 wherein said at least one electrical device further comprises an audio transducer.

6. A fishing lure as set forth in claim 5 wherein said microprocessor further comprises a plurality of programs selectable by a user for providing a predetermined sequence of activation of a light emitting diode, said audio transducer and said vibration motor, said predetermined sequence including pauses.

7. A fishing lure as set forth in claim 2 further comprising at least one attractant pocket in said casement for holding a fish attractant material, with an opening to said at least one attractant pocket so that when the casement is vibrated by said vibration motor, said at least one attractant pocket is also vibrated, increasing a rate of release of said fish attractant material.

8. A fishing lure comprising:
    a body constructed of a soft, plastic material,
    an insert comprising a discrete, separate watertight housing insertable into said soft, plastic material of said body, leaving a tunnel-like aperture in said soft, plastic material of said body after insertion of the housing, said housing containing a power supply, circuitry coupled to said power supply and a plurality of different, electrically operated devices operable by said circuitry, said different, electrically operated devices each having a different function, said devices serving as an attractant to fish when activated,
    a switch activated by immersion in water and deactivated by removal from water and coupled between said power supply and said circuitry for respectively energizing and deenergizing said circuitry to implement a sequence of activation of said devices and to develop an electrical field associated with said fishing lure.

9. A fishing lure as set forth in claim 8 wherein said devices comprise an illumination device, a vibration-producing motor and an audio producing device.

10. A fishing lure as set forth in claim 9 wherein said circuitry further comprises a plurality of programming switches to select one of a plurality of sequences for operating said devices.

11. A fishing lure as set forth in claim 9 further comprising at least one pocket in said body for holding an attractant material, with an opening in said at least one pocket sized for slowly releasing said attractant material in an absence of vibration from said vibration-producing motor and for releasing said attractant material at a faster rate when said vibration-producing motor is energized.

12. A fishing lure as set forth in claim 8 wherein said circuitry further comprises a fixed program of a sequence of events for operating said devices.

13. A fishing lure as set forth in claim 8 further comprising at least one ballast air pocket in said body, and at least one opening communicating with said pocket for admitting air into said at least one ballast pocket or expelling air from said pocket.

14. A method for catching fish with a fishing lure comprising the steps of:
    a) inserting into a solid, soft-bodied fishing lure a single discrete watertight container of a plurality of different, electrically operated, fish attracting devices,
    b) utilizing a single pair of contacts to initiate both operation of said plurality of different, electrically operated, fish attracting devices and provide an electrical field around said lure when said pair of contacts are bridged by water containing electrolytes,
    c) electronically sequencing operation of said plurality of different, electrically operated, fish attracting devices in combination with pauses.

15. A method for catching fish with a fishing lure as set forth in claim 14 further comprising the step of providing, as said plurality of different, electrically operated, fish attracting devices, a light device, a sound device, and a vibration device, and further including scent.

16. A method for catching fish as set forth in claim 15 further comprising the step of increasing a rate at which said scent is dispense by utilizing said vibration device to increase a rate at which said scent is dispensed.

* * * * *